(12) United States Patent
Marquais-Bienewald et al.

(10) Patent No.: US 7,731,761 B2
(45) Date of Patent: Jun. 8, 2010

(54) POLYMERIC HAIR DYES

(75) Inventors: Sophie Marquais-Bienewald, Hegenheim (FR); Olof Wallquist, Bottmingen (CH); Christian Cremer, Lörrach (DE); Beate Fröhling, Grenzach-Wyhlen (DE); Andreas Möck, Rheinfelden (DE)

(73) Assignee: Ciba Corporation, Tarrytown, NY (US)

( * ) Notice: Subject to any disclaimer, the term of this patent is extended or adjusted under 35 U.S.C. 154(b) by 0 days.

(21) Appl. No.: 12/309,300

(22) PCT Filed: Jul. 9, 2007

(86) PCT No.: PCT/EP2007/056945
§ 371 (c)(1),
(2), (4) Date: Jan. 13, 2009

(87) PCT Pub. No.: WO2008/009579
PCT Pub. Date: Jan. 24, 2008

(65) Prior Publication Data
US 2009/0255063 A1  Oct. 15, 2009

(30) Foreign Application Priority Data
Jul. 18, 2006  (EP) ................................. 06117348

(51) Int. Cl.
*A61Q 5/10* (2006.01)
*C07D 213/22* (2006.01)
(52) U.S. Cl. ........................ 8/405; 8/552; 8/554; 8/647; 8/657; 546/264
(58) Field of Classification Search .................... 8/405, 8/552, 647, 657; 546/264
See application file for complete search history.

(56) References Cited

U.S. PATENT DOCUMENTS

| | | | |
|---|---|---|---|
| 3,920,855 A | 11/1975 | Dawson et al. | 426/250 |
| 4,228,259 A | 10/1980 | Kalopissis et al. | 525/435 |
| 4,250,327 A | 2/1981 | Dawson et al. | 560/169 |
| 4,911,731 A * | 3/1990 | Loveless et al. | 8/405 |
| 5,125,930 A * | 6/1992 | Taniguchi | 8/655 |
| 5,708,151 A | 1/1998 | Mockli | 534/608 |
| 2003/0078359 A1 | 4/2003 | Ichinohe | 528/25 |
| 2003/0177591 A1 | 9/2003 | Mockli | 8/405 |
| 2004/0049020 A1 | 3/2004 | Mockli | 534/767 |
| 2004/0143913 A1 | 7/2004 | Mockli et al. | 8/406 |
| 2005/0101690 A1 | 5/2005 | Ichinohe | 523/113 |
| 2006/0026776 A1 | 2/2006 | Mockli | 8/405 |

FOREIGN PATENT DOCUMENTS

JP 2001020186 1/2001

OTHER PUBLICATIONS

STIC Search Report dated Jan. 26, 2010.*
Patent Abstracts of Japan Publication No. 2001020186, Jan. 23, 2001.
Chemical Abstract, vol. 60, No. 9, Apr. 27, 1964 for H. Baumann et al., Chimia, vol. 15, No. 1, pp. 163-168, (1961).

* cited by examiner

*Primary Examiner*—Eisa B Elhilo
(74) *Attorney, Agent, or Firm*—Mervin G. Wood

(57) ABSTRACT

Disclosed are polymeric dyes of formula (1a); (1b); or (1c); wherein A and B, independently from each other represent a polymer backbone; $X_1$ and $X_2$ independently from each other are a linkage group selected from —$C_1$-$C_{10}$alkylene-; —$C_2$-$C_{12}$alkenylene-; —$C_5$-$C_{10}$cycloalkylene-; $C_5$-$C_{10}$arylene; —$C_5$-$C_{10}$arylene-($C_1$-$C_{10}$alkylene)-; —C(O)—; —($CH_2CH_2$—O)$_{1-5}$—; —C(O)O—; —OCO—; —N($R_1$)—; —CON($R_1$)—; —($R_1$)NC(O)—; -O-; —S—; —S(O)—; —S(O)$_2$—; —S(O)$_2$—N($R_1R_2$); or the direct bond; $R_1$ and $R_2$ independently from each other are hydrogen; or unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl); $Y_1$ and $Y_2$ independently from each other are a residue of an organic dye; or hydrogen; wherein at least one of $Y_1$ and $Y_2$ is a residue of an organic dye; $An_1$, $An_2$ and $An_3$, independently from each other are an anion; a and b independently from each other are a number from 1 to 3; m is a number from O to 1000; n is a number from O to 1000; and p is a number from 1 to 1000; wherein the sum of m+n+p≧3.

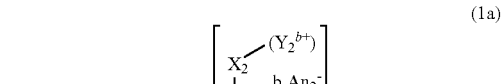

(1a)

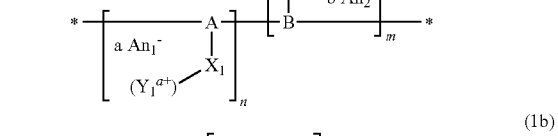

(1b)

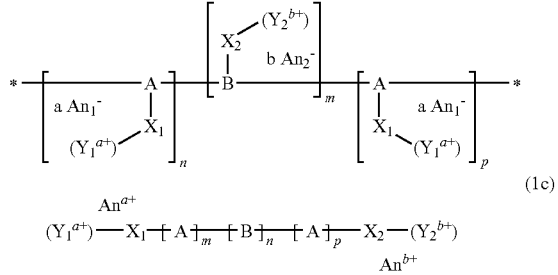

(1c)

25 Claims, No Drawings

POLYMERIC HAIR DYES

The present invention relates to novel polymeric dyes and compositions comprising these compounds, to a process for their preparation and to their use for dyeing of organic materials, such as keratin-containing fibers, wool, leather, silk, cellulose or polyamides.

It is well known that cationic compounds have a good affinity to negative charged hair. These characteristics have been used to contact the hair with small molecules, but also with polymers.

Numerous cationic polymeric dyes have been disclosed for use as a colorant for human hair, for example in U.S. Pat. No. 4,228,259, U.S. Pat. No. 4,182,612 or FR 2 456 764. These references teach that the polymer moiety has the cationic charge.

Surprisingly it was found that very good dyeing results are obtained with polymeric hair dyes wherein the cationic charge is located in dye moiety.

Therefore the present invention relates to polymeric dyes of formula (1a)

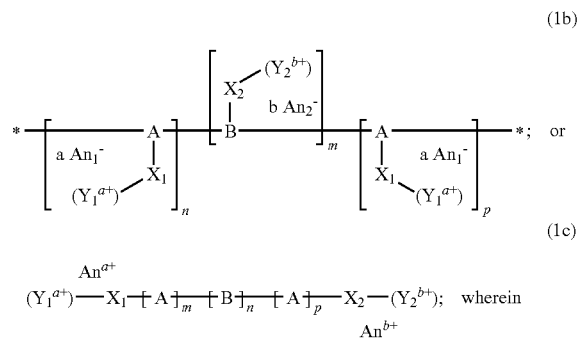

(1c)

$$\text{An}^{a+}$$
$$(Y_1^{a+})\text{---}X_1\text{---}[A]_m\text{---}[B]_n\text{---}[A]_p\text{---}X_2\text{---}(Y_2^{b+}); \text{ wherein}$$
$$\text{An}^{b+}$$

A and B independently from each other represent a polymer backbone;

$X_1$ and $X_2$ independently from each other are a linkage group selected from —$C_1$-$C_{10}$alkylene-; —$C_2$-$C_{12}$alkenylene-; —$C_5$-$C_{10}$cycloalkylene-; $C_5$-$C_{10}$arylene; —$C_5$-$C_{10}$arylene-($C_1$-$C_{10}$alkylene)-; —C(O)—; —(CH$_2$CH$_2$—O)$_{1-5}$—; —C(O)O—; —OCO—; —N(R$_1$)—; —CON(R$_1$)—; —(R$_1$)NC(O)—; —O—; —S—; —S(O)—; —S(O)$_2$—; —S(O)$_2$—N(R$_1$R$_2$)—; or the direct bond;

$R_1$ and $R_2$ independently from each other hydrogen; or unsubstituted or substituted, straight-chain or branched, monocyclic or polycyclic, interrupted or uninterrupted $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_5$-$C_{10}$alkyl($C_5$-$C_{10}$aryl);

$Y_1$ and $Y_2$ independently from each other are a residue of an organic dye; or hydrogen; wherein at least one of $Y_1$ and $Y_2$ is a residue of an organic dye;

$An_1$, $An_2$ and $An_3$, independently from each other are an anion;

a and b independently from each other are a number from 1 to 3;

m is a number from 0 to 1000; and n is a number from 0 to 1000;

p is a number from 1 to 1000;

wherein the sum of m+n+p≧3.

$C_1$-$C_{14}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl, undecy, dodecyl, tredecyl or tetradecyl.

$C_2$-$C_{14}$alkenyl is for example allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, iso-dodecenyl, n-dodec-2-enyl or n-octadec-4-enyl.

$C_6$-$C_{10}$aryl is for example phenyl or naphthyl.

$C_1$-$C_{10}$alkylene is for example methylene, ethylene, propylene, isopropylene, n-butylene, sec-butylene, tert-butylene, n-pentylene, 2-pentylene 3-pentylene, 2,2'-dimethylpropylene, cyclopentylene, cyclohexylene, n-hexylene, n-octylene, 1,1',3,3'-tetramethylbutylene, 2-ethylhexylene, nonylene or decylene.

In formulae (1a), (1b) and (1c) preferably $Y_1$ and $Y_2$ independently from each other are selected from the group of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

More preferably, $Y_1$ and $Y_2$ independently from each other are selected from azo, azomethine, hydrazomethine, merocyanine, methine and styryl dyes.

Most preferably $Y_1$ and $Y_2$ have the same meaning.

Preferably in formulae (1a), (1b) and (1c)

A and B, independently from each other are selected from polymers of monoolefins and di-olefins; mixtures of polymers of monoolefins and diolefins; copolymers of monoolefins and diolefins with each other or with other vinyl monomers; polystyrene, poly(p-methylstyrene), poly(α-methylstyrene); aromatic homopolymers and copolymers derived from vinyl aromatic monomers; copolymers and hydrogenated copolymers of vinyl aromatic monomers and comonomers selected from ethylene, propylene, dienes, nitriles, acids, maleic anhydrides, maleimides, vinyl acetate and vinyl chloride or acrylic derivatives and mixtures thereof; graft copolymers of vinyl aromatic monomers; halogen-containing polymers; polymers derived from α,β-unsaturated acids and derivatives thereof; copolymers derived from α,β-unsaturated acids and derivatives thereof with other unsaturated monomers; polymers derived from unsaturated alcohols and amines or the acyl derivatives or acetals thereof; homopolymers and copolymers of cyclic ethers; polyacetals; polyphenylene oxides and sulfides, and mixtures of polyphenylene oxides with styrene polymers or polyamides; Polyurethanes derived from hydroxyl-terminated polyethers, polyesters or polybutadienes on the one hand and aliphatic or aromatic polyisocyanates on the other, as well as precursors thereof; polyamides and copolyamides derived from diamines and dicarboxylic acids and/or from aminocarboxylic acids or the corresponding lactams; polyureas, polyimides, polyamide-imides, polyetherimids, polyesterimids, polyhydantoins and polybenzimidazoles; polyesters derived from dicarboxylic acids and diols and/or from hydroxycarboxylic acids or the corresponding lactones; polycarbonates and polyester carbonates; polyketones; polysulfones, polyether sulfones and polyether ketones; Crosslinked polymers derived from aldehydes on the one hand and phenols, ureas and melamines on the other hand; polysiloxanes; natural polymers; and blends of the mentioned polymers.

Examples for polymers of monoolefins and diolefins are polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
a) radical polymerisation (normally under high pressure and at elevated temperature).
b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

Mixtures of the polymers mentioned above are for example mixtures of polypropylene with polyisobutylene, polypropylene with polyethylene (for example PP/HDPE, PP/LDPE) and mixtures of different types of polyethylene (for example LDPE/HDPE).

Examples of copolymers of monoolefins and diolefins with each other or with other vinyl monomers are ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in above, for example polypropylene/ethylene-propylene copolymers, LDPE/ethylene-vinyl acetate copolymers (EVA), LDPE/ethyleneacrylic acid copolymers (EAA), LLDPE/EVA, LLDPE/EAA and alternating or random polyalkylene/carbon monoxide copolymers and mixtures thereof with other polymers, for example polyamides.

Homopolymers and copolymers mentioned above may have any stereostructure including syndiotactic, isotactic, hemi-isotactic or atactic; where atactic polymers are preferred. Stereoblock polymers are also included.

Examples of aromatic homopolymers and copolymers derived from vinyl aromatic monomers including styrene are α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

Examples for copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof are for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

Hydrogenated aromatic polymers derived from hydrogenation of polymers mentioned above especially including polycyclohexylethylene (PCHE) prepared by hydrogenating atactic polystyrene, often referred to as polyvinylcyclohexane (PVCH).

Homopolymers and copolymers may have any stereostructure including syndiotactic, isotactic, hemi-isotactic or atactic; where atactic polymers are preferred. Stereoblock polymers are also included.

Examples for graft copolymers of vinyl aromatic monomers are styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

Examples for halogen-containing polymers are polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

Examples for polymers derived from α,β-unsaturated acids and derivatives thereof are polyacrylates and polymethacrylates; polymethyl methacrylates, polyacrylamides and polyacrylonitriles, impact-modified with butyl acrylate.

Examples for copolymers of the monomers mentioned above with each other or with other unsaturated monomers are acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

Examples for polymers derived from unsaturated alcohols and amines or the acyl derivatives or acetals thereof are for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in above.

Examples for homopolymers and copolymers of cyclic ethers are polyalkylene glycols, polyethylene oxide, polypropylene oxide or copolymers thereof with bisglycidyl ethers.

Examples for polyacetals are polyoxymethylene and those polyoxymethylenes which contain ethylene oxide as a comonomer; polyacetals modified with thermoplastic polyurethanes, acrylates or MBS.

Examples for polyamides and copolyamides derived from diamines and dicarboxylic acids and/or from aminocarboxylic acids or the corresponding lactams are polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

Examples for polyesters derived from dicarboxylic acids and diols and/or from hydroxycarboxylic acids or the corresponding lactones are polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.

Examples for crosslinked polymers derived from aldehydes on the one hand and phenols, ureas and melamines on the other hand are phenol/formaldehyde resins, urea/formaldehyde resins and melamine/formaldehyde resins.

Examples for natural polymers are cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

Example for blends of the aforementioned polymers (polyblends) are PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Preferably both the polymer backbone (A and B) and residue of an organic dye ($Y_1$ and $Y_2$) have a functional group selected from the electrophilic group selected from halide, tosylate, mesylate, methoxy, acid chloride, sulfonyl chloride, epoxides, anhydride; or a nucleophilic group selected from amine, hydroxyl and thiol.

Preferably the molecular weight of the polymeric dye is from 400 to 5000.

"Anion" denotes, for example, an organic or inorganic anion, such as halide, preferably chloride and fluoride, sulfate, hydrogen sulfate, phosphate, boron tetrafluoride, carbonate, bicarbonate, oxalate or $C_1$-$C_8$alkyl sulfate, especially methyl sulfate or ethyl sulfate; anion also denotes lactate, formate, acetate, propionate or a complex anion, such as the zinc chloride double salt.

Most preferably are polymeric dyes of formula

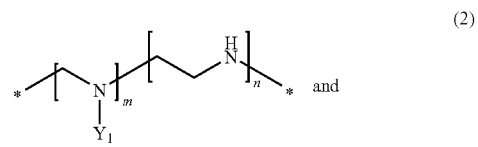

(2)

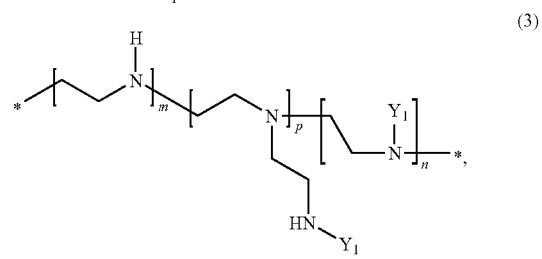

(3)

wherein $Y_1$ is a residue of an organic dye selected from azo, anthrachinone, azomethine, hydrazomethine, merocyanine, methine and styryl dyes; and m, n and p are a number from 0 to 1000; wherein in formula (2) the sum of m and n $\geq$ 3 and wherein in formula (3) the sum of m and n and p $\geq$ 3.

Preferred are also polymeric dyes of formula

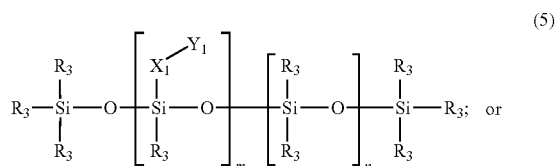

(5)

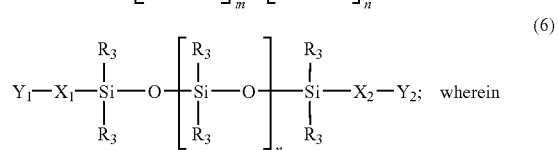

(6)

$R_3$ is $C_1$-$C_5$alkyl; and $X_1, X_2, Y_1, Y_2$, m and n are defined as in formula (1).

Further preferred are also dyes of formula

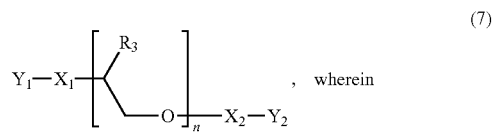

(7)

$R_3$ is $C_1$-$C_5$alkyl; and $X_1, X_2, Y_1, Y_2$ and n are defined as in formula (1).

The dyes of formula (1a), (1b) or (1c) according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties to washing, such as, for example, fastness to light, shampooing and rubbing.

Generally, hair dyeing agents on a synthetic base may be classified into three groups:
  temporary dyeing agents
  semipermanent dyeing agents, and
  permanent dyeing agents.

The multiplicity of shades of the dyes can be increased by combination with other dyes.

Therefore the dyes of formula (1a), (1b) and (1c) of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The dyes of formula (1a), (1b) and (1c) may be used in combination with at least one single direct dye different from the dyes of formula (1a), (1b) and (1c).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

Furthermore, the dyes of formula (1a), (1b) and (1c) may be combined with at least one cationic azo dye, for example the compounds disclosed in GB-A-2 319 776 as well as the oxazine dyes described in DE-A-299 12 327 and mixtures thereof with the other direct dyes mentioned therein.

The dyes of formula (1a), (1b) and (1c) may also be combined with acid dyes, for example the dyes which are known from the international names (Color index), or trade names.

The dyes of formula (1a), (1b) and (1c) may also be combined with uncharged dyes.

Furthermore, the dyes of formula (1a), (1b) and (1c) may also be used in combination with oxidation dye systems.

Furthermore, autooxidizable compounds may be used in combination with the dyes of formula (1a), (1b) and (1c).

The dyes of formula (1a), (1b) and (1c) may also be used in combination with naturally occurring dyes.

Furthermore, the dyes of formula (1a), (1b) and (1c) may also be used in combination with capped diazotised compounds.

Suitable diazotised compounds are for example the compounds of formulae (1)-(4) in WO 2004/019897 (bridging gages 1 and 2) and the corresponding watersoluble coupling components (I)-(IV) as disclosed in the same reference on p. 3 to 5.

The present invention also relates to formulations, which are used for the dyeing of organic materials, preferably keratin-containing fibers, and most preferably human hair, comprising at least one dye of formula (1a), (1b) and (1c).

Preferably the dyes of formula (1a), (1b) and (1c) are incorporated into the composition for treating organic material, preferably for dyeing in amounts of 0.001-5% by weight (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

The dyeing compositions of the present invention are applied on the hair in a temperature range of 25 to 200, preferably 18 to 80, and most preferably from 20 to 40° C.

One preferred embodiment of the present invention relates to the formulation of dyes, wherein the dyes of formula (1a), (1b) and (1c) are in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pretreatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts; for example emulsifiers may be present in the dyeing compositions in concentrations from 0.5 to 30% by weight and thickeners in concentrations of from 0.1 to 25% by weight of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, I. 1 to p. 244, I. 12.

If the dyes of formula (1a), (1b) and (1c) are used together with oxidation dyes and/or the addition salts thereof with an acid, they may be stored separately or together. Preferably the oxidation dyes and the direct dyes which are not stable to reduction are stored separately.

The dyes of formula (1a), (1b) and (1c) may be stored in a liquid to paste-like preparation (aqueous or non-aqueous) or in the form of a dry powder.

When the dyes are stored separately, the reactive components are intimately mixed with one another directly before use. In the case of dry storage, a defined amount of hot (from 50 to 80° C.) water is usually added and a homogeneous mixture prepared before use.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:—non-ionic polymers, cationic polymers, acrylamide/dimethyldiallylammonium chloride copolymers, diethyl-sulfate-quaternised dimethylaminoethyl methacrylate/vinylpyrrolidone copolymers, vinylpyrrolidone/imidazolinium methochloride copolymers; —quaternised polyvinyl alcohol, zwitterionic and amphoteric polymers, anionic polymers, thickeners, structuring agents, hair-conditioning compounds, protein hydrolysates, perfume oils, dimethyl isosorbitol and cyclodextrins, solubilisers, anti-dandruff active ingredients, substances for adjusting the pH value, panthenol, pantothenic acid, allantoin, pyrrolidonecarboxylic acids and salts thereof, plant extracts and vitamins, cholesterol; —light stabilisers and UV absorbers, consistency regulators, fats and waxes, fatty alkanolamides, polyethylene glycols and polypropylene glycols having a molecular weight of from 150 to 50 000, complexing agents, swelling and penetration substances, opacifiers, pearlising agents, propellants, antioxidants, sugar-containing polymers, quaternary ammonium salts and bacteria inhibiting agents.

The dyeing compositions according to the present invention generally comprise at least one surfactant. Suitable surfactants are zwitterionic or ampholytic, or more preferably anionic, non-ionic and/or cationic surfactants.

A further embodiment of the present invention relates to the dyeing of keratin-containing fibers.

The processes comprises
(a) treating the keratin-containing fiber with at least one dye of formula (1a), (1b) and (1c) and
(b) leaving the fiber to stand and then rinsing the fiber.

The dyes of formula (1a), (1b) and (1c) are suitable for all-over dyeing of the hair, that is to say when dyeing the hair on a first occasion, and also for re-dyeing subsequently, or dyeing of locks or parts of the hair.

The dyes of formula (1a), (1b) and (1c) are applied on the hair for example by massage with the hand, a comb, a brush, or a bottle, or a bottle, which is combined with a comb or a nozzle.

In the processes for dyeing according to the invention, whether or not dyeing is to be carried out in the presence of a further dye will depend upon the color shade to be obtained.

Further preferred is a process for dyeing keratin-containing fibers which comprises treating the keratin-containing fiber with at least one dye of formula (1a), (1b) and (1c), a base and an oxidizing agent.

A preferred embodiment for dyeing keratin-containing fibers, in particular human hair, with a dye of formula (1a), (1b) and (1c) and an oxidizing agent, comprises $a_1$) treating the keratin-containing fiber with the oxidizing agent, which optionally contains at least one dye of formula (1a), (1b) and (1c), $b_1$) treating the keratin-containing fiber with an oxidizing agent free composition, which optionally contains at least one dye of formula (1a), (1b) and (1c); or alternatively $a_2$) treating the keratin-containing fiber with an oxidizing agent free composition, which optionally contains at least one dye of formula (1a), (1b) and (1c);

$b_2$) treating the keratin-containing fiber with an oxidizing agent, which optionally contains least one dye of formula (1a), (1b) and (1c), with the proviso that at least in one of the process steps $a_1$), $a_2$), $b_1$) or $b_2$) a dye of formula (1a), (1b) and (1c) is present.

In general, the oxidizing agent containing composition is left on the fiber for 0 to 45 minutes, in particular for 15 to 30 minutes at 15 to 45° C.

The oxidizing agent free composition usually comprises customary adjuvants and additives. Preferred are those, which are described in German Patent Application, in col 3, I. 17 to I. 41.

In general, the dye of formula (1a), (1b) and (1c) and the oxidizing agent free composition are left on the fiber for 5 to 45 minutes, in particular for 10 to 25 minutes at 15 to 50° C.

One preferred embodiment of the process is to wash the hair after dyeing with a shampoo and/or a weak acid, such as citric acid or tartrate acid.

The dyes of formula (1a), (1b) and (1c) which are stable to reduction can be stored together with the oxidizing agent free compositions and may be applied as a single composition.

Advantageously the compositions comprising a dye of formula (1a), (1b) and (1c) which are not stable to reduction are prepared with the oxidizing agent free composition just before the dyeing process.

In a further embodiment, the dye of formula (1a), (1b) and (1c) and the oxidizing agent free composition may be applied simultaneously or in succession.

Customary, the oxidizing agent containing composition is evenly applied in a sufficient amount related to the amount of hair, usually in amounts of 30 to 200 g.

Oxidizing agents are for example persulfate or dilute hydrogen peroxide solutions, hydrogen peroxide emulsions or hydrogen peroxide gels, alkal. earth metal peroxides, organic peroxides, such as urea peroxides, melamine peroxides, or alkalimetalbromat fixations are also applicable if a shading powder on the basis of semi-permanent, direct hair dyes is used.

Further preferred oxidizing agents are
oxidizing agents to achieve lightened coloration, as described in WO 97/20545, especially p. 9, I. 5 to 9,
oxidizing agents in the form of permanent-wave fixing solution, as described in DE-A-19 713 698, especially p. 4, I. 52 to 55, and I. 60 and 61 or EP-A-1062940, especially p. 6, I. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% by weight the corresponding composition.

The oxidizing agents may be present in the dyeing compositions according to the invention preferably in an amount from 0.01% to 6%, especially from 0.01% to 3%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

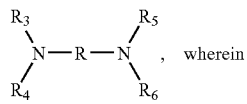, wherein

R is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations-comprising the dyes of formula (1a), (1b) and (1c) on the keratin-containing fiber, preferably the hair is by using a multi-compartment dyeing device or "kit" or any other multi-compartment packaging system, as described for example in WO 97/20545 on p. 4, l. 19 to l. 27.

Generally the hair is rinsed after treatment with the dyeing solution and/or permanent-wave solution.

A further preferred embodiment of the present invention relates to a method of dyeing hair with oxidative dyes, which comprises
a. mixing at least one dye of formula (1a), (1b) and (1c) and optionally at least one coupler compound and at least one developer compound, and an oxidizing agent, which optionally contains at least one further dye, and
b. contacting the keratin-containing fibers with the mixture as prepared in step a.

For adjusting the pH-value organic or inorganic acids, as for example described in DE 199 59 479, col 3, l. 46 to l. 53 are suitable.

Furthermore, the present invention relates to a process of dyeing of keratin-containing fibers of the dyes of formula (1a), (1b) and (1c) with autooxidable compounds and optionally further dyes.

The process comprises
a. mixing at least one autooxidable compound and at least one developer compound and at least one dye of formula (1a), (1b) and (1c) and optionally further dyes, and
b. treating the keratin-containing fiber with the mixture prepared in step a.

Furthermore, the present invention relates to a process for dyeing keratin-containing fibers with the dyes of formula (1a), (1b) and (1c) and capped diazotised compounds, which comprises,
a. treating the keratin-containing fibers under alkaline conditions with at least one capped diazotised compound and a coupler compound, and optionally a developer compound ad optionally an oxidizing agent, and optionally in the presence of a further dye, and optionally with at least one dye of formula (1a), (1b) and (1c), and
b. adjusting the pH in the range of 6 to 2 by treatment with an acid, optionally in the presence of a further dye, and optionally at least one dye of formula (1a), (1b) and (1c), with the proviso that at least in one step a. or b. at least one dye of formula (1a), (1b) and (1c) is present.

The capped diazotised compound and coupler compound and optionally the oxidizing agent and developer compound can be applied in any desired order successively or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

The alkaline dyeing compositions of step a. and the acid dyeing compositions of step b. are left on the fiber for 5 to 60 minutes at 15 to 45° C., in particular for 5 to 45 minutes at 20 to 30° C.

Furthermore, the present invention relates to a process for dyeing keratin-containing fibers with the dyes of formula (1a), (1b) and (1c) and at least one acid dye.

The following examples serve to illustrate the processes for dyeing without limiting the processes thereto. Unless specified otherwise, parts and percentages relate to weight. The amounts of dye specified are relative to the material being dyed.

PREPARATION EXAMPLES

Part A

Polyethylenimine Based

The examples A1 to A28 are prepared by reacting one of the polyethyleneimines PEI 1 to PEI 5 with one of the dyes Dye 1 to Dye 5. The reaction mixtures are worked up by one of the workup procedures 1 to 5. The reaction conditions and workup procedures for each example are given in table 1. The analytical data for the products are given in table 2.

Polyethyleneimines used in examples A1 to A28:

PEI 1 with an average molecular number weight (Mn) of 423 g/mol

PEI 2 with an average molecular number weight of 600 g/mol

PEI 3 with an average molecular number weight of 1200 g/mol

PEI 4 with an average molecular number weight of 1800 g/mol

PEI 5 with an average molecular number weight of 10000 g/mol

Dyes use in examples A1 to A28:

Dye 1: [structure: 1,3-dimethylimidazolium azo-linked to 4-methoxyphenyl, Cl⁻]

Dye 2: [structure: 1,3-dimethylimidazolium azo-linked to 4-fluorophenyl, Cl⁻]

Dye 3: [structure: 1,3-dimethylimidazolium azo-linked to 2-fluorophenyl, Cl⁻]

Dye 4: [structure: N-methyl-N-(2-chloroethyl)aminophenyl-vinyl-pyridinium, methosulfate counterion]

Dye 5: [structure: phenyl-N(Me)-N=CH-pyridinium-CH₂CH(OH)CH₂Cl, acetate counterion]

Dye 6: [structure: phenyl-N(Me)-N=CH-pyridinium-CH₂CH₂CH₂Br, Br⁻]

Workup Procedure 1:
After cooling the reaction mixture is evaporated to dryness. The powder is taken in successively in acetone and dichloromethane, filtered off, washed with the same solvent and dried. Finally the product is dissolved in ethanol and dried again.

Workup Procedure 2:
The reaction mixture is cooled to room temperature and the solvent is evaporated to dryness. The obtained oil is dissolved in methanol and the solution is dropped into acetonitrile. The precipitate is filtered off and dried under vacuum.

Workup Procedure 3:
The reaction mixture is cooled to room temperature, the product is filtered off and dried in vacuum.

Workup Procedure 4:
The reaction mixture is cooled to room temperature and 1 eq. of hydrochloric acid (relative to the amount of dye) is added. The precipitated product is filtered off and dried in vacuum.

Workup Procedure 5:
The reaction mixture is cooled to room temperature and the solvent is evaporated to dryness. The residue is dissolved in ethanol and filtered. The solvent of the filtrate is again evaporated and the remaining product is stirred in isopropanol and dried.

TABLE 1

Table 1: Reaction conditions for the examples A1-A28. Mn (PEI) is the average molecular number weight of the polyethyleneimine. The dye equivalents are given relative to the number of PEI nitrogen atoms.

| Example | Mn (PEI) | Dye | Eq. Dye | Solvent | T [° C.] | Time | Workup Procedure | Yield | Product Color |
|---|---|---|---|---|---|---|---|---|---|
| A1 | 423 | Dye 1 | 0.5 | isoprop. | 55-60 | 23 h | 1 | 104 | red |
| A2 | 423 | Dye 1 | 1 | isoprop. | 60 | 22 h | 2 | 17 | red |
| A3 | 423 | Dye 1 | 1 | water (pH 7-9) | 60 | 50 h | 2 | 15 | red |
| A4 | 423 | Dye 1 | 1 | MeOH | 60 | 24 h | 2 | 13 | red |
| A5 | 423 | Dye 2 | 0.5 | isoprop. | RT | 24 h | 3 | 71 | red |
| A6 | 423 | Dye 2 | 1 | isoprop. | RT | 24 h | 3 | 73 | red |
| A7 | 423 | Dye 1 | 0.5 | isoprop. | 60 | 24 h | 4 | 65 | red |
| A8 | 423 | Dye 1 | 0.25 | isoprop. | 60 | 24 h | 4 | 91 | red |
| A9 | 423 | Dye 1 | 0.1 | isoprop. | 60 | 24 h | 4 | 88 | red |
| A10 | 423 | Dye 1 | 0.5 | water | 40-60 | 24 h | 5 | 58.2 | red |

TABLE 1-continued

Table 1: Reaction conditions for the examples A1-A28. Mn (PEI) is the average molecular number weight of the polyethyleneimine. The dye equivalents are given relative to the number of PEI nitrogen atoms.

| Example | Mn (PEI) | Dye | Eq. Dye | Solvent | T [° C.] | Time | Workup Procedure | Yield | Product Color |
|---|---|---|---|---|---|---|---|---|---|
| | | | | (pH 11.5) | | | | | |
| A11 | 423 | Dye 3 | 0.31 | AcCN | 55 | 24 h | 1 | 130 | violet |
| A12 | 423 | Dye 3 | 0.5 | AcCN | 55 | 24 h | 1 | 122 | violet |
| A13 | 600 | Dye 1 | 1 | MeOH | 60 | 22.5 h | 2 | 23 | red |
| A14 | 600 | Dye 2 | 1 | isoprop. | 40 | 22 h | 3 | 51 | red |
| A15 | 600 | Dye 1 | 0.5 | isoprop. | 60 | 20.5 h | 4 | 23 | red |
| A16 | 1200 | Dye 1 | 0.25 | Isoprop. | 55-60 | 24 h | 1 | 105 | red |
| A17 | 1200 | Dye 1 | 1 | MeOH | 60 | 24 | 2 | 23 | red |
| A19 | 1200 | Dye 2 | 1 | isoprop. | 40 | 22 h | 3 | 47 | red |
| A19 | 1800 | Dye 1 | 0.38 | isoprop. | 55 | | 1 | — | red |
| A20 | 1800 | Dye 1 | 1 | MeOH | 60 | 24 | 2 | 26 | red |
| A21 | 1800 | Dye 2 | 1 | isoprop. | 40 | 22 h | 3 | 45 | red |
| A22 | 10000 | Dye 2 | 1 | isoprop. | 40 | 22 h | 3 | 36 | red |
| A23 | 423 | Dye 4 | 0.5 | EtOH | 78 | 193 h | 2 | 56 | orange |
| A24 | 600 | Dye 5 | 0.5 | BuOH | 60-100 | 25 h | 4 | 28 | yellow |
| A25 | 600 | Dye 5 | 0.1 | BuOH | 100° C. | 21 h | 1.92 | 88 | yellow |
| A26 | 600 | Dye 5 | 0.25 | BuOH | 100° C. | 21 h | 0.86 | 61 | yellow |
| A27 | 423 | Dye 5 | 0.5 | BuOH | 100° C. | 22 h | 0.21 | 12 | yellow |
| A28 | 423 | Dye 6 | 0.1 | $CHCl_3$ | 40° C. | 6 h | 0.07 | 63.6 | yellow |

TABLE 2

Analytical data for examples A1-A28. The ration n(Dye)/n($N_{PEI}$) is the ratio of polymer bound dye molecules to the total number of nitrogen atoms in the polymer

| Example | Mn (GPC-RI) | $\lambda_{max}$ (water) | 1H nmr (D2O), δ (ppm) | n(Dye)/n($N_{PEI}$) |
|---|---|---|---|---|
| A1 | — | 485 nm | 7.9 (m, 2H), 7.5 (m, 2H), 6.9 (m, 2H), 2.6-4.5 (m, 15H), DMSO-d6 | — |
| A2 | 2937 | 490 nm | 6.2-8.1 (br, 6H), 2.6-4.1 (br, 13H) | 0.63 |
| A3 | 1980 | 487 nm | 6.7 (br m, 2H), 7.3 (br m, 2H), 7.8 (br m, 2H) | 0.16 |
| A4 | 3506 | 495 nm | 6.2-8.1 (br, 6H), 2.2-4.9 (br, 13H) | 0.63 |
| A5 | 3145 | 491 nm | 7.7 (m, 2H), 7.3 (m, 2H), 6.8 (m, 1H), 6.6 (m, 1H), 2.6-4.1 (br, 14H) | 0.48 |
| A6 | 3587 | 493 nm | 7.5 (m, 2H), 7.1 (m, 2H), 6.5 (m, 2H), 2.5-3.7 (br, 13H) | 0.61 |
| A7 | 2491 | 486 nm | 7.8 (m, 2H), 7.3 (m, 2H), 6.7 (m, 2H), 2.6-4.1 (br, 13H) | 0.55 |
| A8 | — | 485 nm | 7.8 (m, 2H), 7.3 (m, 2H), 6.8 (m, 2H), 2.8-3.9 (br, 24H) | 0.23 |
| A9 | — | 488 nm | 7.7 (m, 2H), 7.1 (m, 2H), 6.6 (m, 2H), 2.5-3.9 (br, 49H) | 0.09 |
| A10 | — | 494 nm | 7.9 (br, 2H), 7.3 (br, 2H)6.8 (br, 2H), 4.0-2.6 (br, 51H) | 0.09 |
| A11 | — | 520 nm | — | — |
| A12 | — | 527 nm | 7.8 (m, 1H), 7.5-7.7 (m, 3H), 7.15 (m, 1H), 6.85 (m, 1H), 4.1 (m, 6H), 2.6-3.9 (br, 8H), 3.3 (s, 3H) | — |
| A13 | 3605 | 488 nm | 6.5-7.5 (br, 4H), 6.1 (m, 2H), 1.9-3.6 (br, 13H) | 0.55 |
| A14 | 4819 | 494 nm | 7.7 (m, 2H), 7.3 (m, 2H), 6.7 (m, 2H), 2.6-4.0 (br, 14H) | 0.51 |
| A15 | 5240 | 485 (water) | 7.5 (m, 2H), 7.1 (m, 2H), 6.5 (m, 2H), 2.5-3.9 (br, 14H) | 0.48 |
| A16 | — | 489 nm | 7.9 (m, 2H), 7.5 (m, 2H), 6.8 (m, 2H), 4.0 (m, 6H), 2.3-3.5 (br, 17H) in MeOH-d4 | 0.23 |
| A17 | 5341 | 488 nm | 7.5 (m, 2H), 7.1 (m, 2H), 6.4 (m, 2H), 2.4-3.9 (br, 17H) | 0.4 |
| A19 | — | 491 nm | 7.6 (m, 2H), 7.2 (m, 2H), 6.6 (m, 2H), 2.6-4.0 (br, 16H) | 0.4 |
| A19 | 4670 | — | 7.0-8.1 (br, 4H), 6.5 (m, 2H), 2.4-3.9 (br, 17H) | 0.35 |
| A20 | 5548 | 486 nm | 7.0-8.1 (br, 4H), 6.5 (m, 2H), 2.4-3.9 (br, 19H) | 0.32 |

TABLE 2-continued

Analytical data for examples A1-A28. The ration n(Dye)/n(N$_{PEI}$) is the ratio of polymer bound dye molecules to the total number of nitrogen atoms in the polymer

| Example | Mn (GPC-RI) | $\lambda_{max}$ (water) | 1H nmr (D2O), δ (ppm) | n(Dye)/n(N$_{PEI}$) |
|---|---|---|---|---|
| A21 | 7264 | 490 nm | 7.6 (m, 2H), 7.2 (m, 2H), 6.6 (m, 2H), 2.5-4.0 (br, 17H) | 0.36 |
| A22 | 11814 | 488 nm | 7.6 (m, 2H), 7.2 (m, 2H), 6.5 (m, 2H), 2.4-4.0 (br, 16H) | 0.42 |
| A23 | 3259 | 452 nm | 8.3 (m, 2H), 7.5 (m, 6H), 6.7 (m, 2H), 4.0 (m, 3H), 2.4-3.6 (br, 22H) | 0.33 |
| A24 | — | 419 nm | 8.5-6.9 (br, 10H), 2.8-4.6 (br, 22H) | 0.27 |
| A25 | — | 421 nm | 8.5-7.0 (br, 10H), 4.5-2 (br, 52H) | 0.1 |
| A26 | — | 420 nm | 8.5-7.0 (br, 10H), 4.6-2.7 (br, 26H) | 0.2 |
| A27 | — | 423 nm | 8.2-7.1 (br m, 8H), 6.7 (br m, 2H), 4.0-3.2 (br m, 20 H) | 0.28 |
| A28 | — | 419 nm | 8.4-6.9 (br, 10H), 4.4 (br, 2H), 3.5 (s, 3H), 3.3 (br, 2H), 2.8-2.3 (br, 53H), 2.1 (br, 2H) | 0.08 |

Part B

Polysiloxane Based

Example A-29

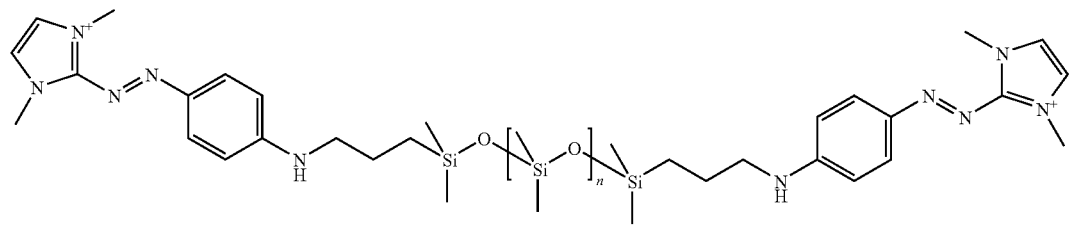

4.75 g of aminopropylterminated polydimethylsiloxane ABCR (0.005 mol) are suspended in 15 ml isopropanol and 2.67 g of 2-(4-Methoxy-phenylazo)-1,3-dimethyl-3-imidazol-1-ium (azo dye A) are added. The reaction mixture is heated to 55° C. for 24 h. After cooling the reaction mixture is dried, taken in 60 ml chloroform and washed 3× with 40 ml water/acetic acid.

The organic phase is dried again giving 6 g of a red powder (Yield 81%).

NMR in CD2Cl2 in ppm: 7.7, br, 2H; 7.3, br, 2H, 6.8, br 2H, 6.2, br, 1H, 3.9, s, 6H, 3.25, s, 2H; 1.7, br, 2H, 0.6, br, 2H; 0, br, 62H $\lambda_{max}$ in MeOH=518 mm

Example A-30

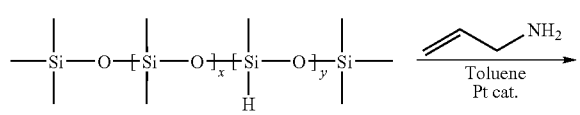

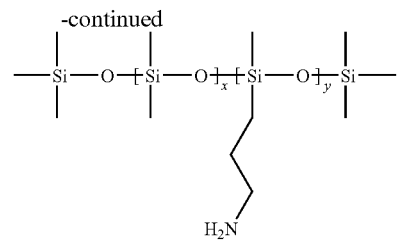

To a solution of 7.5 ml of methylhydrosiloxane-dimethylsiloxane copolymer [68037-59-2] (Gelest HMS 301; MW1900-2000, 25-30 mol % SiH, d=0.98; 30 mmol eq.) in 35 ml of toluene 2.25 ml of allylamine (30 mmol) and 200 µl of platinium (0)-1,3-divinyl-1,1,3,3-tetramethyldisiloxane complex in xylene [68478-92-2]. The reaction mixture is agitated for 3 days at 55° C. and then evaporated to dryness to give 8.85 g polymer.

NMR in DCM in ppm: 2.5 (t, 2H); 1.6 (br, 2H+); 1.4 (br, 2H); 0.4 (t, 2H)

Example A-31

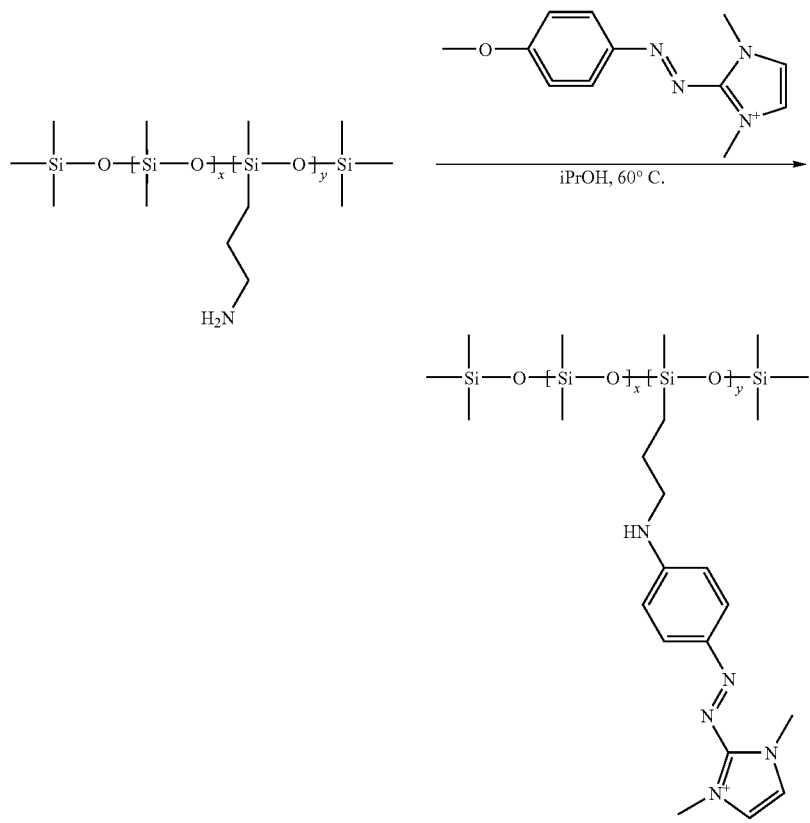

942 mg of polysiloxane A-30 are taken in 15 ml isopropanol and reacted with 1.66 g of 2-(4-Methoxy-phenylazo)-1,3-dimethyl-3-imidazol-1-ium (azo dye A) for 16 h at 60° C. After evaporation of the isopropanol under vacuum, the reaction mixture redissolved in 40 ml DCM (2 min in ultrasonic bath) and 40 ml water (2 min in ultrasonic bath). The emulsion DCM/water is left overnight. The DCM and water phases are separated, leaving a viscous phase which is again treated with DCM and water (same procedure as above). The viscous phase is then taken in 10 ml methanol and dried under vacuum (1 mbar) to give 596 mg of a red solid.

NMR: 1H in MeOH 7.8 (m, 2H), 7.4 (m, 2H), 6.7 (m, 2H), 3.9 (m, 6H), 3.2 (m, MeOH+2H), 1.65 (m, 2H), 0 (m, 30H)

Part C

Polyetherimine Based

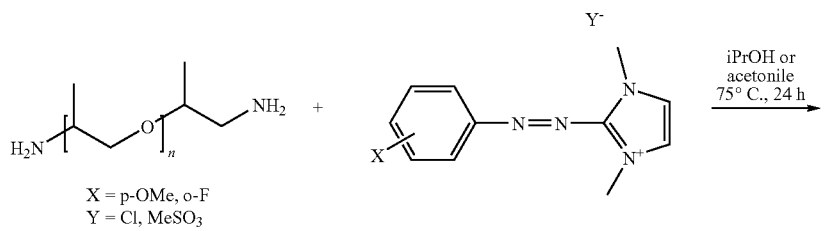

X = p-OMe, o-F
Y = Cl, MeSO$_3$

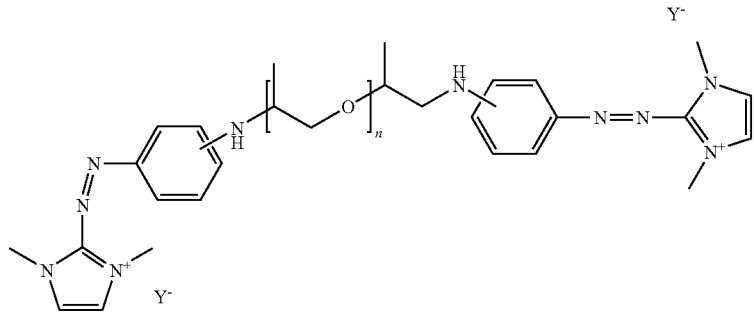

para: A-32
ortho: A-33

Example A-32

Reaction of poly(propyleneglycol)bis(2-aminopropylether) with 2-(4-Methoxy-phenylazo)-1,3-dimethyl-3H-imidazol-1-ium chloride 2 g (0.0044 eq. mol/N) of poly(propyleneglycol)bis(2-aminopropylether) (from Aldrich CAS [9046-10-0] MW 456) are reacted with 2.66 g (0.01 mol) of 2-(4-methoxy-phenylazo)-1,3-dimethyl-3H-imidazol-1-ium chloride in 14 ml isopropanol from 55° to 80° C. for 21 h. After cooling, the reaction mixture is evaporated to dryness, solubilised in 100 ml dichloromethane and washed 3× with 25 ml water and soda to give after evaporation of the organic phase 3.16 g of the expected red polymer (yield 68%).

NMR in DMSO in ppm: 7.4, br, 1H, 7.15, s, 1H, 6.6, br, 1H, 3.75, s, 3H, 3.2-3.7, br, 10H, 1.1, br, 9H $\lambda_{max}$ in MeOH=503 mm

Example A-33

Reaction of poly(propylenglycol)bis(2-aminopropylether), with 2-(2-Fluoro-phenylazo)-1,3-dimethyl-3H-imidazol-1-ium sulfonate 1 g (0.0044 eq. mol/N) of poly(propylenglycol)bis(2-aminopropylether) (from Aldrich CAS [9046-10-0] MW 456) are reacted with 1.92 g (0.0044 mol) of 2-(2-fluoro-phenylazo)-1,3-dimethyl-3H-imidazol-1-ium sulfonate in 6 ml acetonitrile at 75° C. for 24 h. After cooling, the reaction mixture is evaporated to dryness, solubilised in 70 ml dichloromethane and washed 3× with 25 ml water to give after evaporation of the organic phase 1.58 g of the expected violet polymer (yield 67%).

NMR in CH$_2$Cl$_2$ in ppm: 9.3, br 1H; 8, br, 2H, 7.65, d, 1H, 7.4, t, 1H, 6.7, br, 1H, 4.1, s, 6H, 3.1-3.8, br, 23H, 1.3, br, 5H, 0.9-1.1, br, 18H $\lambda_{max}$ in MeOH=531 mm

Example A-34

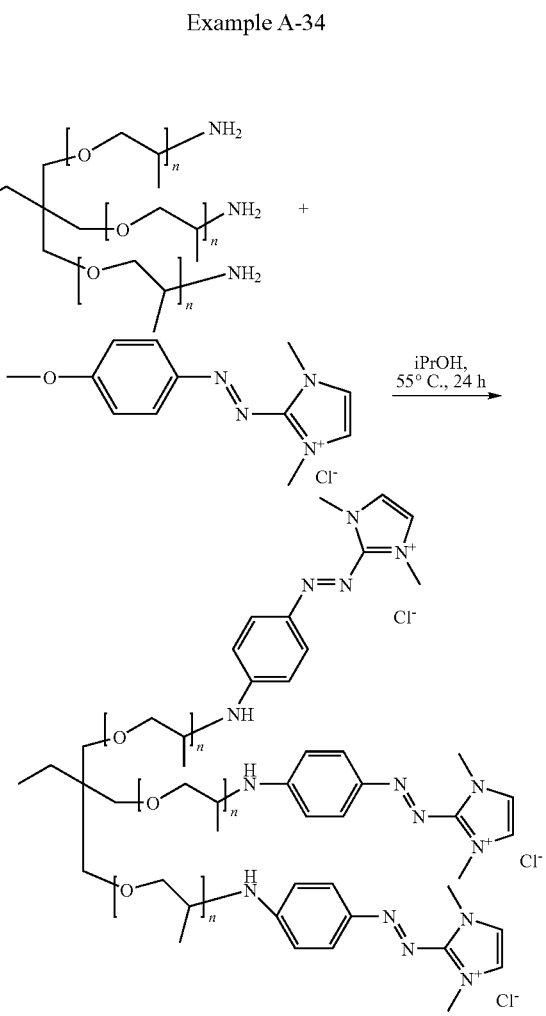

Reaction of Trimethloylpropanetris[poly(propylenglycol)amin terminated]ether with 2-(4-Methoxyphenylazo)-1,3-dimethyl-3H-imidazol-1-ium chloride 1 g (0.00631 mol/N) of trimethloylpropanetris[poly(propylenglycol)amin terminated]ether from Aldrich CAS

[39423-51-3] are reacted with 1.68 g (0.00631 mol) of 2-(4-methoxy-phenylazo)-1,3-dimethyl-3H-imidazol-1-ium chloride in 7 ml isopropanol at 80° C. for 24 h.

After cooling the reaction mixture is evaporated to dryness, solubilised in 70 ml dichloromethane and washed 3× with 25 ml water to give after evaporation of the organic phase 2.23 g of the expected red polymer (yield 90%).

NMR in CD2Cl2 in ppm: 7.6, br, 3H, 6.8, br, 2H, 6.5, br, 2H, 6.3, s, 2H, 2.6-3.9, br, 25H, 0.6-1.4, br, 14H $\lambda_{max}$ in MeOH=518 nm Example A-35

A suspension of 0.5 g copolyglycidylmetacrylate-butylacrylate (1.72 mmol epoxy eq.) in 1 ml acetonitrile and 4 ml isopropanol is heated to 65° C. until dispersion of the polymer.

0.55 g of 2-(N,N'-4-[methyl-(2-methylamino-ethyl)-amino]-phenylazo)-1,3-dimethyl-3H-imidazol-1-ium chloride (1.72 mmol) are then added at 40° C. and the reaction mixture is heated again at 60° C. for 40 h.

After cooling the reaction mixture is evaporated to dryness, taken in brine and the polymer is extracted in dichloromethane.

White salts are filtered off and the organic layer is evaporated and dissolved in methanol. The rest of solid is filtered off and the solution evaporated to give 1 g of a dark red powder.

NMR in MeOD in ppm: 7.9; br, 2H; 7.5, s, 2H; 6.95, br, 2H; 4, br, 12H; 3.5-3-9, br, 3H; 3.1-3.3, br, 6H (+MeOD); 2.7, br, 2H; 2.5, br, 2H; 2.4, br, 4H; 1.6, br, 3H; 0-7-1.5, br, 12H Example A-36

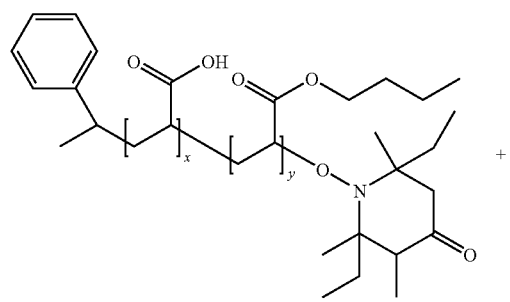

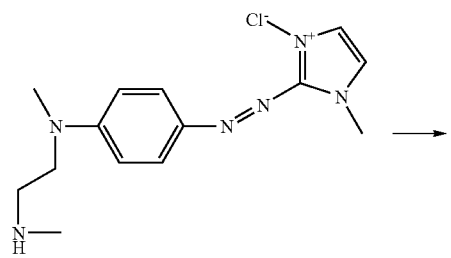

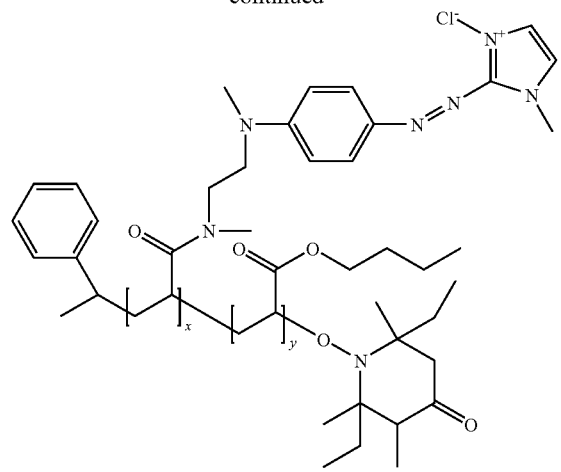

1.06 g copolyacrylic acid-butylacrylate (19.5% solution in dioxan (1.6 mmol eq. COOH)) are diluted in 5 ml acetonitrile.

0.5 g N-ethyl-N'-(3-dimethylaminopropyl)carbodiimide (3.2 mmol) are added and the reaction mixture is cooled to 5° C.

After 45 min 0.52 g 2-(N,N'-4-[methyl-(2-methylamino-ethyl)-amino]-phenylazo)-1,3-dimethyl-3H-imidazol-1-ium chloride (1,6 mmol) and 0.48 g pyridine (4.8 mmol) are added and the reaction mixture is then agitated at room temperature for 18 h.

After evaporation of the solvents the powder is washed with ethylacetate and dried to give 0.74 g of a dark red powder.

NMR in MeOD in ppm: 7.8, br, 2H; 7.5, br, 2H; 6.9, br, 2H; 3.9, br, 8H; 3.6, br, 4H; 2.5-3.4, br, 23H; 0.7-2.0, br, 16H B. Application Examples For the application examples the following hair types have been used:
- 1 blonde hair tress (VIRGIN White Hair),
- 1 middle blonde hair tress (UNA-Europ. nature hair, Color middle blonde),
- 1 bleached hair tress (UNA-Europ. nature hair, Color white bleached).

Coloring Solution:

0.1% w/w of one of the dyes described in examples A1 to A28 were dissolved in a Plantaren solution (10% w/w Plantacare 200UP (ID: 185971.5) in water; pH adjusted to 9.5 with 50% citric acid solution or monoethanolamine solution). For some examples different solvents or solvent mixtures have been used, which are given in Table 3.

The hair tresses are dyed according to the following procedure:

The coloring solution was applied directly to the dry hair, incubated for 20 min. at room temperature, and then rinsed off under tap water (water temperature: 37° C.+/−1° C.; flow rate of water: 5-6 l/min.). Then it is pressed out with a paper towel and dried over night at room temperature on a glass plate.

To determine the wash fastness two sets of hair tresses are dyed under the same conditions. One set of the dyed tresses is washed with a commercial shampoo (GOLDWELL definition Color & Highlights, color-conditioner shampoo) using approx. 0.5 g shampoo for each tress under tap water (water temperature: 37° C.+/−1° C.; flow rate 5-6 l/min). Finally the tresses are rinsed under tap water, pressed out with a paper towel, combed and dried with a hair dryer or at room temperature. This procedure is repeated 10 times.

Then the color loss of the set of washed tresses relative to the set of unwashed tresses is evaluated using the Grey Scale according to: Industrial Organic Pigments by Herbst&Hunger, 2nd ed., p. 61, Nr 10: DIN 54 001-8-1982, "Herstellung und Bewertung der Änderung der Farbe", ISO 105-A02-1993.

TABLE 3

Results for Application Examples B1-B31

| Example | Dye | Solvent | Hair Type | Color | Intensity | Brilliance | Wash-fastness |
|---|---|---|---|---|---|---|---|
| B1 | A1 | Water (pH 6.9) | blond | red | good | good | 3 |
|  |  |  | middle blond | red | good | good | 3 |
|  |  |  | bleached | red | good | good | 3-4 |
| B2 | A1 | Plantaren/Water 4:1 | blond | red | good | good | 3 |
|  |  |  | middle blond | red | good | good | 3 |
|  |  |  | bleached | red | good | good | 3-4 |
| B3 | A2 | Coloring Solution | blond | red | good | good | 4-5 |
|  |  |  | middle blond | red | good | good | 4-5 |
|  |  |  | bleached | red | good | good | 4 |
| B4 | A2 | Plantaren/MeOH 3:1 | blond | red | good | good | 4 |
|  |  |  | middle blond | red | good | good | 4 |
|  |  |  | bleached | red | good | good | 4 |
| B5 | A3 | Coloring Solution | blond | red | good | good | 4-5 |
|  |  |  | middle blond | red | good | good | 4 |
|  |  |  | bleached | red | good | good | 3-4 |
| B6 | A4 | Coloring Solution | blond | red-brown | good | good | 4 |
|  |  |  | middle blond | red-brown | good | good | 4 |
|  |  |  | bleached | red-brown | good | good | 3-4 |
| B7 | A5 | Coloring Solution | blond | red | good | good | 4 |
|  |  |  | middle blond | red | good | good | 4 |
|  |  |  | bleached | red | good | good | 3 |
| B8 | A6 | Coloring Solution | blond | red | good | good | 4 |
|  |  |  | middle blond | red | good | good | 4-5 |
|  |  |  | bleached | red | good | good | 4 |
| B9 | A7 | Plantaren Solution (pH 5.5) | blond | red | good | good | 4-5 |
|  |  |  | middle blond | red | good | good | 4-5 |
|  |  |  | bleached | red | good | good | 4 |
| B10 | A8 | Coloring Solution | blond | red | good | good | 4-5 |
|  |  |  | middle blond | red | good | good | 4 |
|  |  |  | bleached | red | good | good | 3-4 |
| B11 | A9 | Coloring Solution | blond | red | good | good | 4 |
|  |  |  | middle blond | red | good | good | 4-5 |
|  |  |  | bleached | red | good | good | 3-4 |
| B12 | A10 | Coloring Solution | blond | red | good | good | 4-5 |
|  |  |  | middle blond | red | good | good | 3-4 |
|  |  |  | bleached | red | good | good | 4 |
| B13 | A11 | Water (pH 6.9) | blond | violet | good | good | 3 |
|  |  |  | middle blond | violet | good | good | 3-4 |
|  |  |  | bleached | violet | good | good | 3 |
| B14 | A11 | Coloring Solution | blond | violet | good | good | 3-4 |
|  |  |  | middle blond | violet | good | good | 3 |
|  |  |  | bleached | violet | good | good | 3 |
| B15 | A12 | Plantaren/Water 1:1 | blond | violet | good | good | 3 |
|  |  |  | middle blond | violet | good | good | 3 |
|  |  |  | bleached | violet | good | good | 3-4 |
| B16 | A13 | Coloring Solution | blond | red-brown | good | good | 4-5 |
|  |  |  | middle blond | red-brown | good | good | 4-5 |
|  |  |  | bleached | red-brown | good | good | 4 |

TABLE 3-continued

Results for Application Examples B1-B31

| Example | Dye | Solvent | Hair Type | Color | Intensity | Brilliance | Wash-fastness |
|---|---|---|---|---|---|---|---|
| B17 | A14 | Coloring Solution | blond | red-brown | good | good | 3-4 |
| | | | middle blond | red-brown | good | good | 4 |
| | | | bleached | red-brown | good | good | 3-4 |
| B18 | A15 | Coloring Solution | blond | red | good | good | 4 |
| | | | middle blond | red | good | good | 4-5 |
| | | | bleached | red | good | good | 4 |
| B19 | A16 | Water (pH 8.3) | bleached | copper | good | good | 2-3 |
| | | | middle blond | copper | good | good | 3-4 |
| | | | bleached | copper | good | good | 4 |
| B20 | A17 | Coloring Solution | blond | red-brown | good | good | 3-4 |
| | | | middle blond | red-brown | good | good | 4-5 |
| | | | bleached | red-brown | good | good | 3-4 |
| B21 | A19 | Coloring Solution | blond | red-brown | good | good | 3 |
| | | | middle blond | red-brown | good | good | 4-5 |
| | | | bleached | red-brown | good | good | 4 |
| B22 | A19 | Water/Methanol 4:1 | blond | red | good | good | 3 |
| | | | middle blond | red | good | good | 3 |
| | | | bleached | red | good | good | 3 |
| B23 | A20 | Coloring Solution | blond | red-brown | good | good | 4 |
| | | | middle blond | red-brown | good | good | 4-5 |
| | | | bleached | red-brown | good | good | 3-4 |
| B24 | A21 | Coloring Solution | blond | red-brown | good | good | 2-3 |
| | | | middle blond | red-brown | good | good | 4 |
| | | | bleached | red-brown | good | good | 4 |
| B25 | A22 | Coloring Solution | blond | red-brown | good | good | 3 |
| | | | middle blond | red-brown | good | good | 4 |
| | | | bleached | red-brown | good | good | 4 |
| B26 | A23 | Coloring Solution | blond | orange | good | good | 5 |
| | | | middle blond | orange | good | good | 5 |
| | | | bleached | orange | good | good | 4-5 |
| B27 | A24 | Coloring Solution | blond | yellow | good | good | 4 |
| | | | middle blond | yellow | good | good | 4-5 |
| | | | bleached | yellow | good | good | 4 |
| B28 | A25 | Coloring Solution | blond | yellow | good | good | 3-4 |
| | | | middle blond | yellow | good | good | 4 |
| | | | bleached | yellow | good | good | 3 |
| B29 | A26 | Coloring Solution | blond | yellow | good | good | 4 |
| | | | middle blond | yellow | good | good | 4-5 |
| | | | bleached | yellow | good | good | 3-4 |
| B30 | A27 | Coloring Solution | blond | yellow | moderate | moderate | 4-5 |
| | | | middle blond | yellow | moderate | moderate | 4-5 |
| | | | bleached | yellow | moderate | moderate | 3-4 |
| B31 | A28 | Coloring Solution | blond | yellow | good | good | 4 |
| | | | middle blond | yellow | good | good | 4-5 |
| | | | bleached | yellow | good | good | 3-4 |

Example B32

0.1% of compound of formula A-29 is dissolved in a 10% solution of a non-ionic surfactant (Plantacare 200UP, Henkel) adjusted to pH 9.5 using citric acid or monoethanolamine. This red dyeing solution is applied on the dry hair (two blond, two middle blond and two damaged hair strands) and allowed to stand for 20 min at room temperature. Then, the strands are rinsed under tap water and dried 12 h.

Part BB:

Results:

| Hair Type | Color | Intensity | Brillance | Washing Fastness |
|---|---|---|---|---|
| Blond | red | good | good | 1-2 |
| Middle blond | red | good | good | 2-3 |
| Damaged | red | good | good | 3 |

Example B33

0.1% of compound of formula A-31 is dissolved in a 10% solution of a non-ionic surfactant (Plantacare 200UP, Henkel) adjusted to pH 9.5 using citric acid or monoethanolamine. This red dyeing solution is applied on the dry hair (two blond, two middle blond and two damaged hair strands) and allowed to stand for 20 min at room temperature. Then, the strands are rinsed under tap water and dried 12 h.

Part BB:

Results:

| Hair Type | Color | Intensity | Brillance | Washing Fastness |
|---|---|---|---|---|
| Blond | red | moderate | moderate | 3 |
| Middle blond | red | good | good | 3-4 |
| Damaged | red | good | good | 3 |

Examples B34-B36

0.1% of compound of formula A32-, A-33 and A-34 respectively are dissolved in a 10% solution of a non-ionic surfactant (Plantacare 200UP, Henkel) adjusted to pH 9.5 using citric acid or monoethanolamine. This red or violet dyeing solution is applied on the dry hair (two blond, two middle blond and two damaged hair strands) and allowed to stand for 20 min at room temperature. Then, the strands are rinsed under tap water and dried 12 h.

Results:

| Compound of formula | Polymer type | Hair Type | Color | Intensity | Brillance | Washing Fastness |
|---|---|---|---|---|---|---|
| A-32 | linear | Blond | red | good | good | 3 |
|  |  | Middle blond | red | good | good | 4-5 |
|  |  | bleached | red | good | good | 4 |
| A-33 | linear | Blond | violet | good | good | 4 |
|  |  | Middle blond | violet | good | good | 4-5 |
|  |  | bleached | violet | good | good | 4 |
| A-34 | branched | Blond | red | good | good | 4 |
|  |  | Middle blond | red | good | good | 4 |
|  |  | bleached | red | good | good | 4 |

Examples B60-B70

0.1% of compound of formula A-35 and A-36 respectively are dissolved in a 10% solution of a non-ionic surfactant (Plantacare 200UP, Henkel) adjusted to pH 9.5 using citric acid or monoethanolamine.

This red or violet dyeing solution is applied on the dry hair (two blond, two middle blond and two damaged hair strands) and allowed to stand for 20 min at room temperature. Then the strands are rinsed under tap water and dried 12 h.

| Compound of formula | Hair Type | Color | Intensity | Brillance | Washing Fastness |
|---|---|---|---|---|---|
| A-35 | Blond | red | good | good | 3 |
|  | Middle blond | red | good | good | 3 |
|  | bleached | red | good | good | 3 |
| A-36 | Blond | red | good | good | 3 |
|  | Middle blond | red | good | good | 3-4 |
|  | bleached | red | good | good | 3 |

Mixtures of Polymeric Dyes:

A dye emulsion, pH=10.5

| INGREDIENT | w/w % |
|---|---|
| Mixture of dyes as described in table 4, 5 and 6 | x |
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Deionized Water 70° C. | ad 100.00 | is mixed with 1.5 weight of 9% hydrogen peroxide solution and the mixture is immediately applied to a tress of brown hair. After 30 minutes the tress is rinsed, shampooed, rinsed and dried. The color of the dyed tresses is given in Table 4.

TABLE 4

Mixtures of two polymeric dyes

| Comp. of formula | Color | B37 | B38 | B39 | B40 | B41 | B42 | B43 | B44 |
|---|---|---|---|---|---|---|---|---|---|
| A24 | yellow | | 0.05 | 0.3 | | | | | |
| A27 | yellow | 0.05 | | | | 0.05 | | 0.1 | |
| A23 | orange | 0.05 | | | | 0.05 | | 0.1 | 0.5 |
| A7 | red | | 0.05 | 0.1 | 0.05 | | 0.05 | | |
| A11 | violet | | | | 0.05 | | 0.05 | | 0.5 |
| Total dye content X | | 0.1 | 0.1 | 0.4 | 0.1 | 0.1 | 0.1 | 0.2 | 1.0 |
| Color result on bleached hair[1] | | C | O | O | B | R | B | C | B |

[1] C = copper, O = orange, B = brown, R = red

TABLE 5

Mixtures of three polymeric dyes.

| Comp. of formula | Color | B45 | B46 | B47 | B48 | B49 |
|---|---|---|---|---|---|---|
| A27 | yellow | 0.1 | 0.07 | | 0.07 | 0.03 |
| A23 | orange | 0.1 | 0.02 | 0.4 | 0.07 | 0.03 |
| A7 | red | | | 0.3 | 0.01 | 0.03 |
| A11 | violet | 0.1 | 0.1 | 0.1 | 0.03 | |
| Total dye content X | | 0.3 | 0.19 | 0.8 | 0.11 | 0.09 |
| Color result on bleached hair[1] | | S | B | B | B | B |

[1] S = black, B = brown

TABLE 6

Mixtures of polymeric and direct dyes.

| Comp. of formula | Color | B50 | B51 | B52 | B53 | B54 | B55 | B56 | B57 |
|---|---|---|---|---|---|---|---|---|---|
| A27 | yellow | | 0.1 | 0.5 | 0.3 | 0.4 | | | |
| A7 | red | 0.2 | | | | | 0.2 | 0.1 | |
| A11 | violet | | | | | | | | 0.2 |
| Direct Dye | | | | | | | | | |
| Basic Yellow 57 | | | | | | | 0.2 | | |
| Basic Red 76 | | | | | 0.1 | | 0.1 | | |
| HC Red No. 3 | | | | 0.1 | | | | 0.1 | |
| HC Red BN | | | 0.1 | | | | | 0.1 | 0.1 |
| Basic Brown 16 | | 0.1 | | | | 0.5 | | | |
| Basic Brown 17 | | 0.1 | | | | 0.5 | | | |
| Basic Blue 7 | | | | | | 0.01 | | | |
| Basic Blue 99 | | 0.1 | | | | 1.0 | | | |
| Total dye content X | | 0.5 | 0.2 | 0.6 | 0.4 | 2.41 | 0.5 | 0.3 | 0.3 |
| Color result on bleached hair[1] | | B | O | O | O | B | R | O | R |

[1] O = orange, B = brown, R = red

Example B58

A dye emulsion (pH=9.8), containing 1% of the dye A16 and; pH=9.8

| | |
|---|---|
| Cetylstearylalcohol | 11.00 |
| Oleth-5 | 5.0 |
| Oleic acid | 2.5 |
| Stearic acid monoethanolamide | 2.5 |
| Coco fatty acid monoethanolamide | 2.5 |
| Sodium laurylsulphate | 1.7 |
| 1,2-Propanediol | 1.0 |
| Ammoniumchloride | 0.5 |
| EDTA, Tetrasodiumsalt | 0.2 |
| Perfume | 0.4 |
| Cornproteinhydrolysate | 0.2 |
| Silica | 0.1 | is mixed with the same weight of 6% hydrogen peroxide solution and the mixture is immediately applied to a tress of brown hair. After 30 minutes the tress is rinsed, shampooed, rinsed and dried. The tress has been dyed red.

Example B59

A dye emulsion, containing
0.1% of the dye A16 and
3.5% Cetearyl alcohol
1.0% Ceteareth 30
0.5% Glycol Distearate
3.0% Stearamide DEA
1.0% Sodium Oleoamphohydroxypropyl Sulfonate
0.5% Polyquarternium-6 and
water ad 100% is applied for 30 minutes, at room temperature to bleached human hair, and rinsed. The result is a red dyeing with good fastnesses.

Example B60

A dye emulsion containing

| | |
|---|---|
| Cetearyl Alcohol | 12.000 |
| Ceteareth-25 | 5.000 |
| Glyceryl Stearate SE | 2.500 |
| Glycol Distearate | 0.500 |
| Polysorbate 60 | 0.500 |
| Oleth-10 | 2.000 |
| Cetearyl Octanoate | 0.750 |
| Deionized Water 70° C. | 72.400 |
| Disodium EDTA | 0.050 |
| Ccompound A1 | 0.900 |
| Monoethanolamine 99% | 1.000 |
| Hydrolyzed Wheat Protein 20% | 1.000 |
| Monoethanolamine 99% | ~0.900 |
| Fragrance Drom 854 148 Linden Blossom | 0.500 |
| pH-Value: 9.90-10.40 | | is applied for 30 minutes, at room temperature, to middle blond human hair, and rinsed. The result is a red dyeing with good fastnesses.

Example B61

60 ml of part A, 60 ml of part B and 3 ml of part C are mixed in a mixing bowl or applicator bottle and the mixture is immediately applied to a tress of brown hair. After 30 minutes the tress is rinsed, shampooed, rinsed and dried. The tress has been dyed in an intensive red.

Shade: Pure Red

|  | INGREDIENT | w/w % |
|---|---|---|
| Part A | Deionized Water RT | 20.00 |
|  | Sodium Sulfite | 0.60 |
|  | Disodium EDTA | 0.05 |
|  | Cocamidopropyl Betaine 30% | 4.00 |
|  | Propylene Glycol | 2.50 |
|  | Monoethanolamine 99% | 1.00 |
|  | Toluene-2,5-Diamine Sulfate | 0.25 |
|  | p-Aminophenol | 0.50 |
|  | 4-Amino-2-Hydroxytoluene | 0.70 |
|  | 2-Methyl-5-Hydroxyethylaminophenol | 0.50 |
|  | 2-Amino-4-Hydroxyethyl AA Sulfate | 0.10 |
|  | Erythorbic Acid | 0.40 |
|  | Deionized Water RT | 43.55 |
|  | Hydroxyethylcellulose - Natrosol 250 HHR CG | 0.75 |
|  | Deionized Water RT | 10.00 |
|  | Isopropyl Alcohol | 8.00 |
|  | Oleth-10 | 1.00 |
|  | Oleic Acid | 1.10 |
|  | Lactamide MEA | 1.00 |
|  | Fragrance Drom 837 375 Tropical Fever | 0.50 |
|  | Dihydroxypropyl PEG-5 Linoleammonium Chloride | 0.50 |
|  | Hydrolyzed Soy Protein | 0.50 |
|  | Monoethanolamine 99% | ~2.50 |
|  | Total: | 100.00 |
| Part B: Developer 6% | Deionized Water RT | 80.50 |
|  | Disodium Phosphate | 0.15 |
|  | Salcare SC80 | 5.00 |
|  | Glycerin 99% | 1.00 |
|  | Sodium Laureth Sulfate 27% | 1.00 |
|  | Etidronic Acid 60% | ~0.35 |
|  | Hydrogen Peroxide 50% | 12.00 |
|  | Total: | 100.00 |
| Part C | Deionized Water RT | 97.18 |
|  | Compound A16 | 1.00 |
|  | Total: | 100.00 |

Example B62

A dye emulsion (pH 10.5), containing 1% of the dye A16; pH=10.5

| INGREDIENT | w/w % |
|---|---|
| Cetearyl Alcohol | 12.00 |
| Ceteareth-20 | 4.50 |
| Polysorbate 60 | 2.30 |
| Glyceryl Stearate SE | 2.00 |
| Sorbitan Stearate | 0.75 |
| Oleth-5 | 1.25 |
| Caprylic/Capric Triglyceride | 0.50 |
| Deionized Water 70° C. | 66.65 |
| Disodium EDTA | 0.05 |
| Monoethanolamine 99% | 0.90 |
| Ammonium Hydroxide 29% | 6.60 |
| Dihydroxypropyl PEG-5 Linoleammonium Chloride | 0.50 |
| Hydrolyzed Soy Protein 20% | 0.50 |
| Fragrance Drom 847 735 - Day at the Beach | 0.50 |
| Total: | 100.00 | is mixed with 1.5 weight of 9% hydrogen peroxide solution and the mixture is immediately applied to a tress of brown hair. After 30 minutes the tress is rinsed, shampooed, rinsed and dried. The tress has been dyed in an intensive red.

Example B63

A dye emulsion, containing 1% of the dye A16 and

| INGREDIENT | w/w % |
|---|---|
| Deionized Water RT | 64.68 |
| Acrylates/C10-30 Alkyl Acrylate Crosspolymer | 0.55 |
| Sodium Hydroxide 25% | 0.03 |
| DMDM Hydantoin | 0.50 |
| Sodium Cocoamphoacetate 32% | 15.00 |
| Ococamidopropyl Betaine 30% | 3.00 |
| Decyl Glucoside | 3.00 |
| Polyquaternium-7 | 0.50 |
| PEG-15 Copolyamine | 0.50 |
| PEG-75 Lanolin | 0.50 |
| Deionized Water RT | 10.00 |
| Disodium EDTA | 0.05 |
| Basic Orange 31 | 0.08 |
| Basic Yellow 87 | 0.01 |
| Basic Red 51 | 0.01 |
| PEG-40 Hydrogenated Castor Oil | 0.95 |
| Fragrance Drom 837 375 Tropical Fever | 0.45 |
| Citric Acid 25% Solution | ~0.20 |
| Total: | 100.00 | is applied for 30 min, at room temperature, to blond human hair, and rinsed.

The result is a very attractive vibrant red dyeing with good fastnesses.

Example B64

A tress of blond hair is shampooed with a shampoo, containing 0.1% of the dye A16 and

| Disodium PEG-5 Laurylcitrate Sulfosuccinate, Sodium Laureth Sulfate | 8.25% |
|---|---|
| Sodium Cocoamphoacetate | 20.9% |
| Methoxy PEG/PPG-7/3 Aminopropyl Dimethicone | 0.5% |
| Hydroxypropyl Guar hydroxypropyltrimonium Chloride | 0.3% |
| PEG-200 Hydrogenated Glyceryl Palmate; PEG-7 Glyceryl Cocoate | 2.5% |
| PEG-150 Distearate | 0.5% |
| Citric Acid (30%) | 2.2% |
| Perfume; Preservatives | q.s. |
| Water | Ad 100% |

After 5 minutes the tress is rinsed and dried. The tress has been dyed red.

Example B65

A conditioner containing 0.1% of the dye A16 and

| Cetyl Alcohol | 3.00% |
|---|---|
| Ceterareth-25 | 0.50% |
| Distearyldimonium Chloride | 1.00% |
| Quaternium-80 | 0.50% |
| Citric Acid | Ad pH = 5 |
| Perfumes; Preservatives | q.s. |
| Water | Ad 100% | is applied to a tress of shampooed blond hair. After 15 min the tress is rinsed and dried. The tress has been dyed red.

Example B66

A conditioner containing 0.1% of the dye A16 and

| Cetyl Alcohol | 3.00% |
| Ceterareth-20 | 0.50% |
| Hydroxypropyl Guar, Hydroxypropyltrimonium chloride | 1.00% |
| Quaternium-80 | 0.50% |
| Citric Acid | Ad pH = 5 |
| Octocrylene | 0.1 |
| Butyl Methoxybibenzoylmethane | 0.1 |
| Perfumes; Preservatives | q.s. |
| Water | Ad 100% | is applied to a tress of shampooed blond hair. After 15 min the tress is rinsed and dried. The tress has been dyed red.

Example B66

A conditioner containing 0.1% of the dye A16 and

| Cetaryl Alcohol, Sodium Cetearyl Sulfate | 3.00% |
| Ceterareth-25 | 0.50% |
| Distearyldimonium Chloride | 1.00% |
| Quaternium-80 | 0.50% |
| Citric Acid | Ad pH = 5 |
| Camphor Benzalkonium Methosulfate | 0.1 |
| Ethyl Salicylate | 0.1 |
| Perfumes; Preservatives | q.s. |
| Water | Ad 100% | is applied to a tress of shampooed blond hair. After 15 min the tress is rinsed and dried. The tress has been dyed red.

Example B67

A conditioner containing 0.1% of the dye A16 and

| Cetyl Alcohol | 3.00% |
| Ceterareth-25 | 0.50% |
| Distearyldimonium Chloride | 1.00% |
| Quaternium-80 | 0.50% |
| Citric Acid | Ad pH = 5 |
| Dimethicone | 0.9 |
| Phenyltrimethicone, Silicone Quaternium-15, Laureth-4 (Polysil 1849) | 2.5 |
| Polysilicone-15 | 0.8 |
| Perfumes; Preservatives | q.s. |
| Water | Ad 100% | is applied to a tress of shampooed blond hair. After 15 min the tress is rinsed and dried. The tress has been dyed red.

Example B68

A dye emulsion, containing
0.1% of the dye A16 and
3.5% Cetearyl alcohol
1.0% Ceteareth 80
0.5% Glycol Distearate
3.0% Stearamide DEA
1.0% Sodium Oleoamphohydroxypropyl Sulfonate
0.5% Polyquarternium-6
0.2% Disodium distyrylbiphenyl disulfonate and
water ad 100% is applied for 30 minutes, at room temperature to bleached human hair, and rinsed. The result is a red dyeing with good fastnesses

The invention claimed is:

1. Polymeric dye of formula

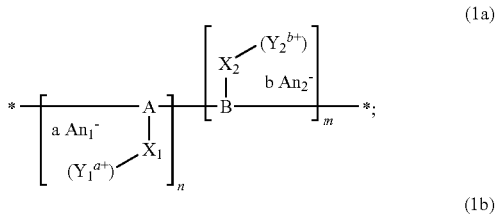

(1a)

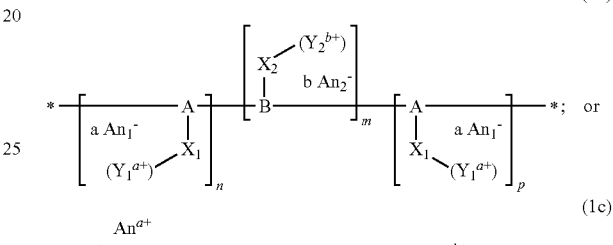

(1b)

$$(Y_1^{a+}) \text{—} X_1 \text{—} \overline{\{A\}_m} \text{—} \overline{\{B\}_n} \text{—} \overline{\{A\}_p} \text{—} X_2 \text{—} (Y_2^{b+}); \quad \text{wherein}$$
$$An^{b+}$$

(1c)

A and B, independently from each other represent a polymer backbone;

$X_1$ and $X_2$ independently from each other are a linkage group selected from the group consisting of —
$C_1$-$C_{10}$alkylene-; —$C_2$-$C_{12}$alkenylene-; —$C_5$-$C_{10}$cycloalkylene-; $C_5$-$C_{10}$arylene;
—$C_5$-$C_{10}$arylene-($C_1$-$C_{10}$alkylene)-; —C(O)—;
—(CH$_2$CH$_2$—O)$_{1-5}$—; —C(O)O—; —OCO—;
—N(R$_1$)—; —CON(R$_1$)—;
—(R$_1$)NC(O)—; —O—; —S—; —S(O)—;
—S(O)$_2$—; —S(O)$_2$—N(R$_1$R$_2$); and the direct bond;

R$_1$ and R$_2$ independently from each other are hydrogen; or unsubstituted or substituted, straight-chain or branched, monocyclic or polycyclic, interrupted or uninterrupted C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_5$-C$_{10}$alkyl(C$_5$-C$_{10}$aryl);

Y$_1$ and Y$_2$ independently from each other are a residue of an organic dye; or hydrogen; wherein at least one of Y$_1$ and Y$_2$ is a residue of an organic dye;

An$_1$, An$_2$ and An$_3$, independently from each other are an anion;

a and b independently from each other are a number from 1 to 3;

m is a number from 0 to 1000;

n is a number from 0 to 1000; and p is a number from 1 to 1000;

wherein the sum of m+n+p≧3.

2. Dye according to claim 1, wherein

Y$_1$ and Y$_2$ independently from each other are selected from the group consisting of anthraquinone, acridine, azo, azamethine, hydrazomethine, triphenylmethane, benzodifuranone, coumarine, diketopyrrolopyrrol, dioxazine, diphenylmethane, formazane, indigoid indophenol, naphthalimide, naphthoquinone, nitroaryl, merocyanine, methine oxazine, perinone, perylene, pyrenequinone, phtalocyanine, phenazine, quinoneimine, quinacridone, quinophtalone, styryl, stilbene, xanthene, thiazine and thioxanthene dyes.

3. Dye according to claim 2, wherein
$Y_1$ and $Y_2$ independently from each other are selected from the group consisting of anthraquinone, azo, azomethine, hydrazomethine, merocyanine, methine and styryl dyes.

4. Dye according to claim 1, wherein $Y_1$ and $Y_2$ have the same meaning.

5. Dye according to claim 1, wherein
A and B, independently from each other are selected from the group consisting of polyethylenimine, polypropylenimine, polyvinylamine; polyvinylimine; polysiloxane; polystyrene, polyvinylimidazol, polyvinylpyridine, polyDADMAC, polyvinylalcohol, polyacrylate, polymethacrylate; polyurethanes derived from hydroxyl-terminated polyethers, polyesters, polybutadienes, aliphatic polyisocyanates, aromatic polyisocyanates; polyamides and copolyamides derived from diamines and dicarboxylic acids and/or from aminocarboxylic acids or the corresponding lactams; polysaccharide, starch, cellulose, lignin; and copolymers and blends of the mentioned polymers.

6. Dye according to claim 1, wherein both the polymer backbone (A and B) and residue of an organic dye ($Y_1$ and $Y_2$) have a functional group selected from the group consisting of halide, tosylate, mesylate, methoxy, acid chloride, sulfonyl chloride, epoxides, anhydride, amine, hydroxyl and thiol.

7. Dye according to claim 1, wherein the molecular weight of the polymeric dye is from 400 to 5000.

8. Dye according to claim 1, which corresponds to formula

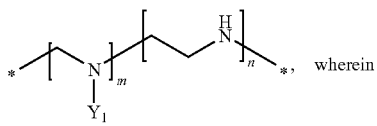

(2)

wherein $Y_1$ is a residue of an organic dye selected from the group consisting of azo, azomethine, hydrazomethine, merocyanine, methine and styryl dyes; and m and n are a number from 0 to 1000; wherein the sum of m and n $\geq$ 3.

9. Dye according to claim 1, which corresponds to formula

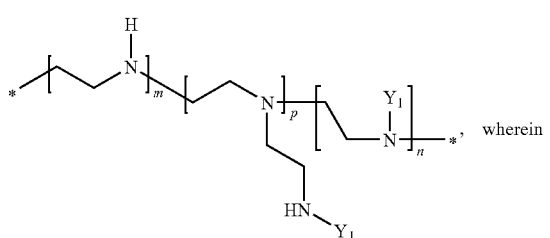

(3)

wherein $Y_1$ is a residue of an organic dye selected from the group consisting of azo, azomethine, hydrazomethine, merocyanine, methine and styryl dyes; and m, n and p are a number from 0 to 1000; wherein the sum of m, n and p $\geq$ 3.

10. Dye according to claim 1, which corresponds to formula

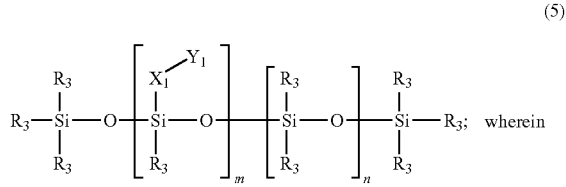

(5)

wherein $R_3$ is $C_1$-$C_5$alkyl; and
$X_1, X_2, Y_1, Y_2$, m and n are defined as in claim (1).

11. Dye according to claim 1, which corresponds to formula

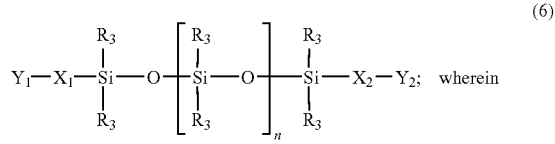

(6)

wherein $R_3$ is $C_1$-$C_5$alkyl; and
$X_1, X_2, Y_1, Y_2$ and n are defined as in claim (1).

12. Dye according to claim 1, which corresponds to formula

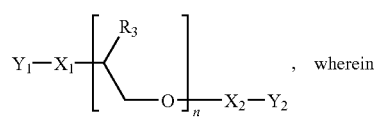

(7)

wherein $R_3$ is $C_1$-$C_5$alkyl; and
$X_1, X_2, Y_1, Y_2$ and n are defined as in claim 1.

13. A composition comprising at least one dye of formula (1a), (1b) or (1c) as defined in claim 1.

14. A composition according to claim 13 comprising in addition at least one single further direct dye and/or an oxidative agent.

15. A composition according to claim 13 in form of a shampoo, a conditioner, a gel or an emulsion.

16. A method of dyeing an organic material, which comprises treating the organic material with at least one dye of formula (1a), (1b) or (1c) according to claim 1.

17. A method according to claim 16, which comprises treating the organic material with at least one dye of formula (1a), (1b) or (1c) and an oxidative agent and, optionally, a further direct dye.

18. A method according to claim 16, which comprises treating the organic material with at least one compound of formula (1a), (1b) or (1c) and at least one single oxidative dye, or treating the organic material with a dye of formula (1a), (1b) or (1c) and at least one single oxidative dye and an oxidative agent.

19. A method according to claim 16 wherein the organic material is selected from keratin-containing fibers.

20. A method according to claim 19 wherein the keratin-containing fiber is human hair.

21. A method of dyeing an organic material, which comprises treating the organic material with a composition according to claim 13.

22. A method according to claim 21, which comprises treating the organic material with said composition and an oxidative agent and, optionally, a further direct dye.

23. A method according to claim 21, which comprises treating the organic material with said composition and at least one single oxidative dye, or treating the organic material with said composition and at least one single oxidative dye and an oxidative agent.

24. A method according to claim 21 wherein the organic material is selected from keratin-containing fibers.

25. A method according to claim 24 wherein the keratin-containing fiber is human hair.

* * * * *